(12) United States Patent
Shen et al.

(10) Patent No.: US 9,522,276 B2
(45) Date of Patent: Dec. 20, 2016

(54) ACCELEROMETER INTEGRITY ALERT

(71) Applicant: Medtronic, Inc., Minneapolis, MN (US)

(72) Inventors: Xiaonan Shen, Shoreview, MN (US); Nathan A Grenz, Shoreview, MN (US); Robert D Musto, Champlin, MN (US); David L Palkert, Golden Valley, MN (US); Jonathan P Roberts, Coon Rapids, MN (US); James D Reinke, Maple Grove, MN (US); Paul R Solheim, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 22 days.

(21) Appl. No.: 14/603,070

(22) Filed: Jan. 22, 2015

(65) Prior Publication Data

US 2016/0213934 A1    Jul. 28, 2016

(51) Int. Cl.
| | |
|---|---|
| *A61N 1/00* | (2006.01) |
| *A61N 1/365* | (2006.01) |
| *A61N 1/37* | (2006.01) |
| *B81C 1/00* | (2006.01) |
| *G01P 15/00* | (2006.01) |

(52) U.S. Cl.
CPC ......... *A61N 1/36542* (2013.01); *A61N 1/3706* (2013.01); *B81C 1/00968* (2013.01); *G01P 15/00* (2013.01)

(58) Field of Classification Search
CPC .... A61N 1/36542; A61N 1/3706; A61N 1/36; A61N 1/36128; A61N 1/36578; G01P 15/00
See application file for complete search history.

(56) References Cited

U.S. PATENT DOCUMENTS

| | | | |
|---|---|---|---|
| 4,485,813 | A | 12/1984 | Anderson et al. |
| 5,052,388 | A | 10/1991 | Sivula et al. |
| 5,593,431 | A | 1/1997 | Sheldon |
| 6,044,297 | A | 3/2000 | Sheldon et al. |
| 6,937,900 | B1 | 8/2005 | Pianca et al. |
| 7,031,772 | B2 | 4/2006 | Condie et al. |
| 7,152,474 | B2 | 12/2006 | Deb et al. |
| 7,340,956 | B2 | 3/2008 | Deb et al. |
| 8,215,151 | B2 | 7/2012 | Sammoura et al. |
| 8,352,030 | B2 | 1/2013 | Denison |
| 8,386,042 | B2 | 2/2013 | Yudovsky et al. |
| 8,433,409 | B2 | 4/2013 | Johnson et al. |

(Continued)

FOREIGN PATENT DOCUMENTS

| | | |
|---|---|---|
| DE | 102014108515 A1 | 12/2014 |
| EP | 2805913 A1 | 11/2014 |
| WO | 2008039242 A1 | 4/2008 |

OTHER PUBLICATIONS (PCT/US2016/013921) PCT Notification of Transmittal of the International Search Report and the Written Opinion of the International Searching Authority, mailed May 23, 2016, 9 pages.

*Primary Examiner* — Mallika D Fairchild
(74) *Attorney, Agent, or Firm* — Evans M. Mburu

(57) ABSTRACT

A medical device and associated method determine a signal amplitude of a sensor signal produced by a MEMS sensor, compare the signal amplitude to a stiction detection condition, detect stiction of the MEMS sensor in response to the signal amplitude meeting the stiction detection condition, and automatically provide a corrective action in response to detecting the stiction.

25 Claims, 6 Drawing Sheets

(56) References Cited

U.S. PATENT DOCUMENTS

| | | |
|---|---|---|
| 8,541,131 B2 | 9/2013 | Lund et al. |
| 2005/0074741 A1* | 4/2005 | Lee .................... A61B 5/0031 |
| | | 434/433 |
| 2008/0081958 A1 | 4/2008 | Denison et al. |
| 2012/0172892 A1 | 7/2012 | Grubac et al. |
| 2013/0035748 A1 | 2/2013 | Bonner et al. |

* cited by examiner

ACCELEROMETER INTEGRITY ALERT

TECHNICAL FIELD

The disclosure relates to implantable medical devices having an accelerometer and automatic detection of a loss of a reliable accelerometer signal.

BACKGROUND

Numerous implantable medical devices (IMDs) are available for acute or chronic implantation within patients. Some implantable medical devices may be used to monitor physiological signals of the patient, such as cardiac pacemakers, implantable hemodynamic monitors, implantable cardioverter defibrillators implantable cardiac monitors (sometimes referred to as implantable loop recorders or ECG monitors), etc. Among the various types of physiological sensors utilized by medical devices for monitoring patients are electrodes for measuring electrical signals and/or impedances, accelerometers, pressure sensors, pH sensors, temperature sensors, oxygen sensors and more.

The physiological signals may be stored, processed and analyzed by the medical device to generate physiological data about a patient useful to a clinician in diagnosing a condition or planning medical treatment. Some implantable devices may be configured to deliver a therapy in conjunction with monitoring of physiological signals. Physiological signals may be processed and analyzed to determine when a therapy is needed or how a therapy needs to be adjusted to benefit the patient. Therapies delivered by an IMD can include electrical stimulation therapies, e.g., cardiac pacing, cardioversion/defibrillation shock pulses, or neurostimulation, and pharmacological or biological fluid delivery therapies.

In order to provide reliable physiological data needed for determining a medical risk, detecting pathological conditions, controlling automatic therapy delivery or generally producing data in a form useful to a clinician for diagnosis, prognosis, and therapy management, reliable sensor signals are required. For example, patient activity level may be determined from an accelerometer signal in order provide rate responsive pacing at a heart rate that meets the metabolic demand of the patient and may be used to assess patient's daily activity levels for evaluating overall patient well-being.

SUMMARY

In general, the disclosure is directed to automatic techniques for detecting or predicting a loss of a reliable signal from an accelerometer included in a medical device. A medical device operating in accordance with the techniques disclosed herein detects reliable signal loss due to stiction of an accelerometer based on a diagnostic analysis of the accelerometer signal.

In one example, the disclosure provides a method performed by a medical device comprising a MEMS sensor, the method comprising determining a signal amplitude of a sensor signal produced by the MEMS sensor, comparing the signal amplitude to a stiction detection condition, detecting stiction of the MEMS sensor in response to the signal amplitude meeting the stiction detection condition and automatically providing a corrective action in response to detecting the stiction.

In another example, the disclosure provides a medical device, comprising a MEMS sensor configured to produce a sensor signal, a control module configured to determine a signal amplitude of the sensor signal, compare the signal amplitude to a stiction detection condition, detect stiction of the MEMS sensor in response to the signal amplitude meeting the stiction detection condition; and provide a corrective action in response to detecting the stiction.

In another example, the disclosure provides a non-transitory, computer readable storage medium comprising a set of instructions that, when executed by a control module of a medical device comprising a MEMS sensor, cause the device to determine a signal amplitude of a sensor signal produced by the MEMS sensor, compare the signal amplitude to a stiction detection condition, detect stiction of the MEMS sensor in response to the signal amplitude meeting the stiction detection condition, and provide a corrective action in response to detecting the stiction.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

Techniques are disclosed herein for automatically detecting sensor signal error due to stiction in a micro-electrical mechanical system (MEMS) sensor, such as in a MEMS accelerometer in an IMD. Detection of signal error due to stiction may be used to automatically predict or detect an unreliable accelerometer and provide an appropriate response. An accelerometer implemented in an IMD for monitoring patient motion, e.g., physical activity, heart motion, muscle motion, lung motion, diaphragm motion, etc., may be implemented MEMS accelerometer. The term "stiction" may be used to generally refer to the static friction that moving parts must overcome in order to be set in motion. In a MEMS accelerometer or other MEMS sensor having moving parts, stiction may cause signal error if the moving parts are unable to overcome static friction when motion is imparted on the sensor. Stiction may prevent the accelerometer from moving and generating a signal correlated to the imparted motion and therefore may result in loss of reliable motion sensing capability by the IMD. The loss of a reliable accelerometer signal may prevent the IMD from functioning as intended. As used herein, the term "detect stiction" refers to detecting the inability of the MEMS sensor to overcome static friction to produce a reliable signal.

An IMD having a MEMS sensor is disclosed herein. The IMD is configured to detect stiction and provide an appropriate response, which may include generating an alert indicating that the integrity of the sensor signal may be compromised and/or adjusting a monitoring and/or therapy delivery control parameter.

Techniques disclosed herein are described in the context of an IMD. It is recognized however that the disclosed techniques may be implemented in an external medical device, such as a wearable medical device, that includes a MEMS sensor such as an accelerometer for monitoring motion of a patient. Furthermore, it is understood that the techniques disclosed herein for detecting stiction may be implemented in other types of MEMS sensors besides accelerometers that include moving parts that need to overcome static friction forces, such as MEMS pressure sensors, gyroscopes or microphones.

Figure 1:
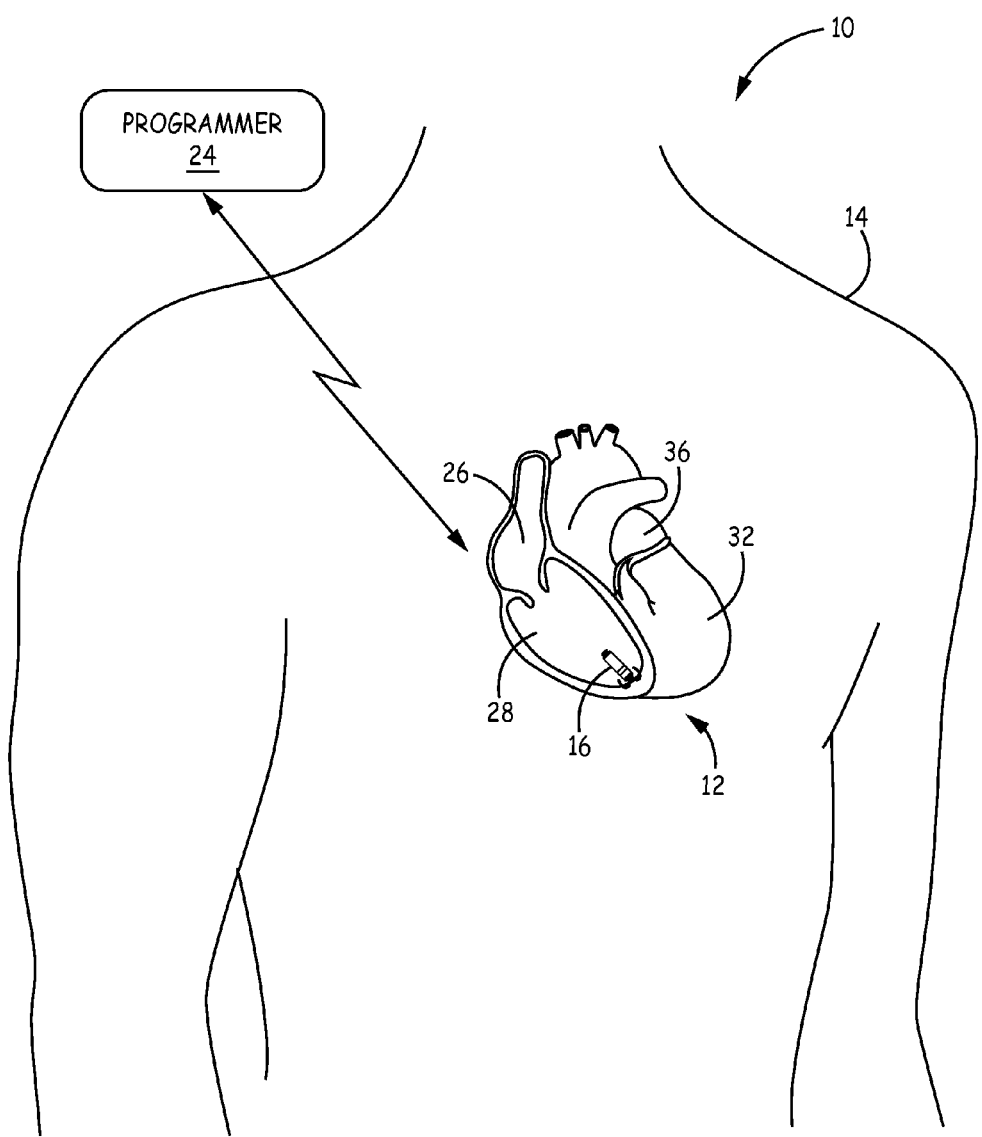
FIG. 1 is a conceptual diagram illustrating a medical monitoring and therapy delivery system that may be used to monitor one or more physiological parameters of a patient and/or to provide therapy to the patient.

FIG. 1 is a conceptual diagram illustrating a medical monitoring and therapy delivery system 10 that may be used to monitor one or more physiological parameters of patient 14 and/or to provide therapy to heart 12 of patient 14. Therapy system 10 includes IMD 16, configured to communicate wirelessly with programmer 24. IMD 16 is shown as an intracardiac pacemaker that is capable of providing electrical signals to heart 12 via one or more electrodes (not shown in FIG. 1) on its outer housing. Additionally, IMD 16 may sense cardiac electrical signals attendant to the depolarization and repolarization of heart 12 via the electrodes on its outer housing. In some examples, IMD 16 provides pacing pulses to heart 12 based on the cardiac electrical signals sensed within heart 12.

In the example of FIG. 1, IMD 16 is positioned wholly within heart 12 proximate to an inner wall of right ventricle (RV) 28 to provide RV pacing. Although IMD 16 is shown within heart 12 particularly in the RV 28 in the example of FIG. 1, IMD 16 may be positioned at any other location outside or within heart 12. For example, IMD 16 may be positioned outside or within right atrium 26, left atrium 36, and/or left ventricle 32, e.g., to provide respective right atrial, left atrial, or left ventricular sensing and pacing.

Depending on the location of implant, IMD 16 may include other stimulation functionalities. For example, IMD 16 may provide atrioventricular nodal stimulation, fat pad stimulation, vagal stimulation, or other types of neurostimulation. In other examples, IMD 16 may be a monitor that senses one or more parameters of heart 12 for patient monitoring purposes and may not provide any stimulation or therapy delivery functionality. In some examples, system 10 may include a plurality of intracardiac IMDs 16, e.g., to provide stimulation and/or sensing at a variety of locations.

IMD 16 is equipped with an accelerometer. In some examples, IMD 16 is a rate-responsive pacemaker having an accelerometer for sensing motion of patient 14 due to physical activity. In such examples, the accelerometer may be referred to as an activity sensor because the accelerometer produces a signal correlated to patient physical activity and the associated metabolic demand of patient 14. IMD 16 determines a sensor-indicated pacing rate based on the accelerometer signal controlling a rate of pacing pulses delivered to heart 12 that meets the patient's metabolic demand.

In some examples, IMD 16 includes a multi-axis accelerometer capable of producing motion signals along two or more different axes. For example, the accelerometer may be a three-dimensional accelerometer producing signals corresponding to motion in three orthogonal axes, x, y and z. The IMD 16 may be configured to select at least one axis for monitoring patient activity. The IMD 16 may be configured to use the multi-axis accelerometer to determine the posture of patient 14.

FIG. 1 further depicts programmer 24 in wireless communication with IMD 16. Programmer 24 may be located in a hospital or clinic and used by a clinician to program operating parameters in IMD 16. In other examples, programmer 24 may be a handheld computing device, computer, or networked computing device. Programmer 24 includes a user interface that presents information to and receives input from a user. It should be noted that the user may also interact with programmer 24 remotely via a networked computer or communication device.

A user, such as a physician, technician, surgeon, electrophysiologist, other clinician, or patient, interacts with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD 16 such as sensing or therapy delivery control parameters. A user may use programmer 24 to retrieve information from IMD 16 regarding the rhythm of heart 12, trends therein over time, or arrhythmic episodes. The user may use programmer 24 to retrieve information from IMD 16 regarding the accelerometer, e.g., relating to the performance of the accelerometer or recorded episodes of the accelerometer signal.

IMD 16 and programmer 24 are configured to communicate via wireless communication. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24. In other examples, IMD 16 and programmer 24 may communicate using distance telemetry that does not require the use of a programming head.

While a single-chamber intracardiac pacemaker is shown in FIG. 1, it is recognized that techniques disclosed herein may be implemented in numerous types of IMDs or combinations of IMDs configured for monitoring a patient and/or delivering a therapy. Techniques disclosed herein may be applied to any medical device having a MEMS-type accelerometer or other sensor that has moving parts subject to stiction. An accelerometer may be included in ECG monitors, hemodynamic monitors, pacemakers, implantable cardioverter defibrillators, neurostimulators, drug delivery pumps, or other medical devices that are implantable or worn by a patient.

Figure 2A:
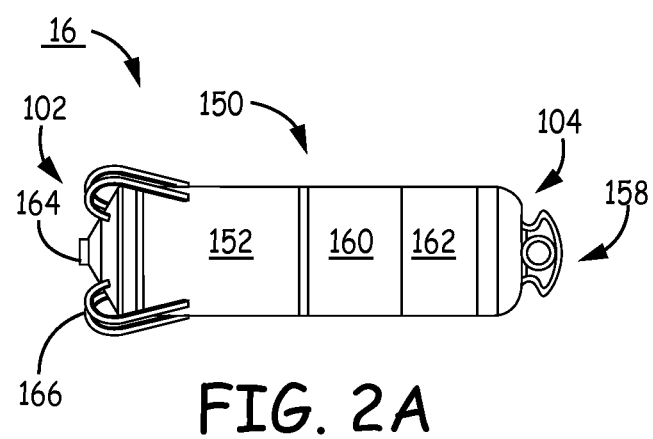
FIG. 2A is a conceptual diagram of the IMD shown in FIG. 1.

FIG. 2A is a conceptual diagram of IMD 16 shown in FIG. 1. IMD 16 includes electrodes 162 and 164 spaced apart along the housing 150 of IMD 16 for sensing cardiac EGM signals and delivering pacing pulses. Electrode 164 is shown as a tip electrode extending from a distal end 102 of pacemaker 16, and electrode 162 is shown as a ring electrode along a mid-portion of housing 150, for example adjacent proximal end 104. Distal end 102 is referred to as "distal" in that it is expected to be the leading end as it advanced through a delivery tool, such as a catheter, and placed against a target pacing site.

Electrodes 162 and 164 form a cathode and anode pair for bipolar cardiac pacing and sensing. Electrodes 162 and 164 may be positioned on or as near as possible to respective proximal and distal ends 104 and 102 to increase the inter-electrode spacing between electrodes 162 and 164. In alternative embodiments, pacemaker 16 may include two or more ring electrodes, two tip electrodes, and/or other types of electrodes exposed along pacemaker housing 150 for delivering electrical stimulation to heart 12 and for sensing EGM signals. Electrodes 162 and 164 may be positioned at locations along pacemaker 16 other than the locations shown. Electrodes 162 and 164 may be, without limitation, titanium, platinum, iridium or alloys thereof and may include a low polarizing coating, such as titanium nitride, iridium oxide, ruthenium oxide, or platinum black, among others.

Housing 150 is formed from a biocompatible material, such as a stainless steel or titanium alloy. In some examples, the housing 150 may include an insulating coating. Examples of insulating coatings include parylene, urethane, PEEK, or polyimide among others. The entirety of the housing 150 may be insulated, but only electrodes 162 and 164 uninsulated.

The housing 150 includes a control electronics subassembly 152, which houses an accelerometer for sensing motion signals as well as the electronics for sensing cardiac electrical signals, producing pacing pulses and controlling therapy delivery and other functions of IMD 16. Housing 150 further includes a battery subassembly 160, which provides power to the control electronics subassembly 152. Battery subassembly 160 may include features of the batteries disclosed in commonly-assigned U.S. Pat. No. 8,433,409 (Johnson, et al.) and U.S. Pat. No. 8,541,131 (Lund, et al.), both of which are hereby incorporated by reference herein in their entirety.

IMD 16 may include a set of fixation tines 166 to secure IMD 16 to or against cardiac tissue, e.g., by interacting with the ventricular trabeculae. Fixation tines 166 are configured to anchor IMD 16 to position electrode 164 in operative proximity to a targeted tissue for delivering therapeutic electrical stimulation pulses. Numerous types of active and/or passive fixation members may be employed for anchoring or stabilizing IMD 16 in an implant position. IMD 16 may include a set of fixation tines as disclosed in commonly-assigned, pre-grant publication U.S. 2012/0172892 (Grubac, et al.), hereby incorporated herein by reference in its entirety.

IMD 16 may further include a delivery tool interface 158. Delivery tool interface 158 may be located at the proximal end 104 of IMD 16 and is configured to connect to a delivery device, such as a catheter, used to position pacemaker 16 at an implant location during an implantation procedure, for example within a heart chamber. A reduced size of IMD 16 enables implantation wholly within a heart chamber in some examples.

Figure 2B:
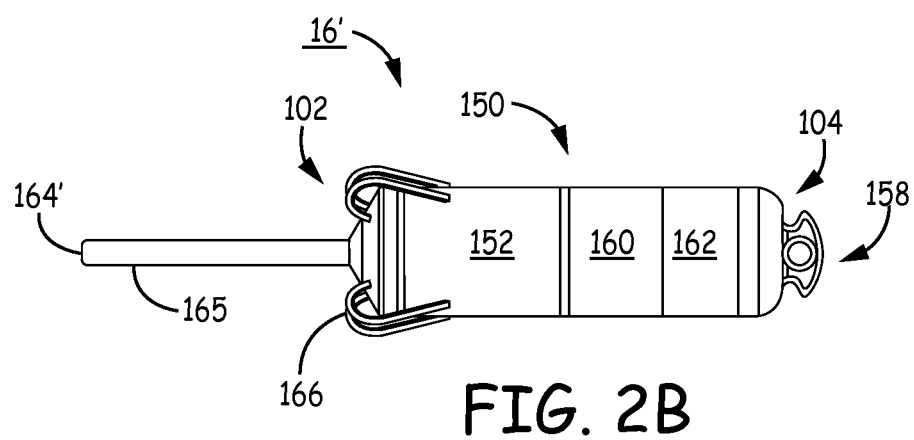
FIG. 2B is a conceptual diagram of another example of an IMD.

FIG. 2B is a conceptual diagram of an alternative embodiment of an IMD 16' having extender 165 coupled to the distal end 102 of pacemaker housing 150 to extend distal electrode 164' away from electrode 162 positioned along housing 150 near or at proximal end 104. Extender 165 shown in FIG. 2B is an insulated electrical conductor that electrically couples electrode 164' to electronic circuitry within housing 150 via an electrical feedthrough crossing housing 150. IMD 16' having an insulated, electrically conductive extender 165 for increasing the inter-electrode spacing may correspond generally to the implantable device and flexible conductor disclosed in commonly-assigned, pre-grant U.S. Publication No. 2013/0035748 (Bonner, et al.), hereby incorporated herein by reference in its entirety. In other examples, a conductive extender 165 may extend from the proximal end 104 of IMD 16. A conductive extender 165 may carry either or both of electrodes 162 and/or 164.

An accelerometer associated with IMD 16' may be enclosed within housing 150 or carried by extender 165. Techniques disclosed herein may be implemented in IMDs having an accelerometer positioned within the IMD outer housing, along an outer surface of the housing, within a connector block coupled to the housing, sometimes referred to as a "header" and having bores for receiving medical electrical leads, or carried by an electrical lead extending from the IMD.

Figure 3:
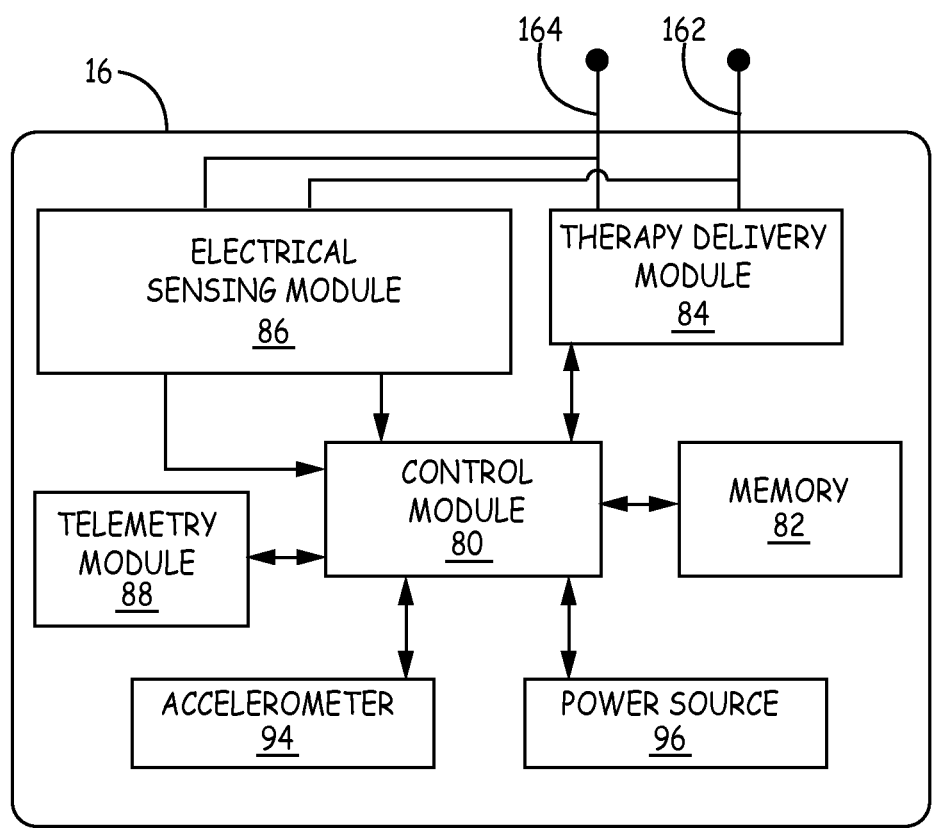
FIG. 3 is a functional block diagram of an example configuration of the IMD of FIG. 1.

FIG. 3 is a functional block diagram of an example configuration of IMD 16. IMD 16 includes a control module 80, memory 82, therapy delivery module 84, electrical sensing module 86, and telemetry module 88. IMD 16 additionally includes accelerometer 94 for detecting patient body motion, e.g., for monitoring patient activity or heart motion. Accelerometer 94 may be a single axis accelerometer for monitoring motion in one axis. In other examples, accelerometer 94 is a multi-axis accelerometer capable of monitoring motion along two or more axes. The techniques described herein for detecting a loss of a reliable accelerometer signal assume that multiple axes are available, however it is recognized that the techniques may readily be used with a single axis accelerometer.

Accelerometer 94 may be implemented as a MEMS device or other motion sensor that may fail to produce a reliable motion signal due to stiction. For example, under normal operating conditions, a beam or other moving element of accelerometer 94 may come into contact and adhere to another MEMS surface. At the micrometer scale of MEMS elements, electrostatic and/or Van der Waals and hydrogen bonding forces become significant. The surface of a moving part of accelerometer 94 may adhere to another accelerometer surface due to such forces, preventing motion of the moving part and leading to accelerometer signal error due to stiction. Detection of accelerometer signal error due to this type of condition is referred to herein as "detecting stiction."

Accelerometer 94 is shown schematically within IMD 16; however it is recognized that an accelerometer 94 may additionally or alternatively be carried by a conductive extender 165, a medical electrical lead extending from IMD 16 or mounted along the exterior of the IMD electronic subassembly 152. A MEMS accelerometer that may be A power source 96 provides power to each of the other modules and components of IMD 16 as required. Control module 80 may execute power control operations to control when various components or modules are powered to perform various IMD functions. Power source 96 may include one or more energy storage devices, such as one or more rechargeable or non-rechargeable batteries. The connections between power source 96 and control module 80 and other IMD modules and components are not shown for the sake of clarity. Power source 96 may provide accelerometer 94 with an input voltage or current signal to bias the accelerometer baseline output signal. As motion is imparted on accelerometer 94, an output signal that varies over a positive and negative output range is received by control module 80 for use in monitoring motion. As described below, the output signal from accelerometer 94 when supplied with a normal input current (or voltage) signal to enable motion monitoring is analyzed for detecting a loss of accelerometer signal reliability. The normal input signal does not itself produce motion of MEMS accelerometer components and does not cause a time-varying signal that appears as motion to the control module.

IMD 16 may include any discrete and/or integrated electronic circuit components that implement analog and/or digital circuits capable of producing the functions attributed to IMD 16 herein. For example, sensing module 86 and control module 80 may include analog circuits, e.g., amplification circuits, filtering circuits, and/or other analog circuitry for receiving and processing signals from electrodes 162 and 164, and accelerometer 94. Electrical sensing module 86, therapy delivery module 84, telemetry module 88 and control module 80 may also include digital circuits, e.g., combinational or sequential logic circuits, memory devices, ND converters, etc., for processing received signals.

The functions attributed to IMD 16 herein may be embodied as one or more processors, hardware, firmware, software, or any combination thereof. Control module 80 may include any one or more of a microprocessor, a controller, a digital signal processor (DSP), an application specific integrated circuit (ASIC), a field-programmable gate array (FPGA), or equivalent discrete or integrated logic circuitry. Depiction of different features of IMD 16 as discrete modules or components is intended to highlight different functional aspects and does not necessarily imply that such modules must be realized by separate hardware or software components. Rather, functionality associated with one or more modules may be performed by separate hardware or software components, or integrated within common or separate hardware or software components.

Memory 82 may include computer-readable instructions that, when executed by control module 80, cause IMD 16 and control module 80 to perform various functions attributed throughout this disclosure to IMD 16. The computer-readable instructions may be encoded within memory 82. Memory 82 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media with the sole exception being a transitory propagating signal.

As used herein, the term "module" refers to an application specific integrated circuit (ASIC), an electronic circuit, a processor (shared, dedicated, or group) and memory that execute one or more software or firmware programs, a combinational logic circuit, state machine, or other suitable components that provide the described functionality. The particular form of software, hardware and/or firmware employed to implement the functionality disclosed herein will be determined primarily by the particular system architecture employed in the IMD system 10 and by the particular detection and therapy delivery methodologies employed by the IMD system 10. Providing software, hardware, and/or firmware to accomplish the described functionality in the context of any modern IMD system, given the disclosure herein, is within the abilities of one of skill in the art.

Electrical sensing module 86 receives cardiac electrical signals from electrodes 162 and 164 for sensing cardiac electrical events, e.g., P-waves and R-waves, in order to monitor electrical activity of heart 12. Sense event signals produced by sensing module 86 are used by control module 80 to determine a need for therapy delivery. Control module 80 may also receive multi-bit digital signals from electrical sensing module 86 and analyze the digital signals for detecting a patient condition, controlling a therapy delivered by therapy delivery module 84, and/or storing patient data in memory 82 for later transmission to programmer 24 via telemetry module 88.

Control module 80 receives an accelerometer signal from accelerometer 94 for monitoring the patient and may use the accelerometer signal for controlling therapy delivery module 84 for delivering a pacing therapy, e.g., rate-responsive bradycardia pacing, according to patient need. Control module 80 includes a therapy control module that controls therapy delivery module 84 to deliver electrical stimulation therapy, e.g., cardiac pacing, to heart 12 according to a selected one or more therapy programs, which may be stored in memory 82. Therapy delivery module 84 may include a pulse generator that is electrically coupled to electrodes 162 and 164, to deliver electrical stimulation therapy to heart 12. Therapy delivery module 84 delivers cardiac pacing pulses according to therapy control parameters and responsive to signals sensed by electrical sensing module 86 and accelerometer 94. Memory 82 stores intervals, counters, or other data used by control module 80 to control the delivery of pacing pulses by therapy delivery module 84. In one example, IMD 16 is a rate responsive pacemaker that utilizes a patient activity metric derived by control module 80 from a signal received from accelerometer 94 for controlling a rate of pacing pulses delivered by therapy delivery module 84.

Control module 80 may also be configured to perform diagnostic testing of IMD 16, which may include monitoring the remaining charge of power source 96 and providing a replacement or recharge indicator, for example. Diagnostic analysis is performed to detect a loss of a reliable accelerometer signal 94. As described below, control module 80 analyzes a signal received from accelerometer 94 to detect stiction and for predicting or detecting a loss of a reliable accelerometer signal.

Accelerometer 94 may be bonded to an inner surface of the control electronics enclosure or incorporated on an internal substrate. Accelerometer 94 may be a one-dimensional accelerometer configured to move in between a maximum positive excursion and a minimum negative excursion, e.g., in a teeter-totter, back-and-forth or other configuration, in response to patient motion in that axis. In other examples, accelerometer is a multi-axis accelerometer including three one-dimensional accelerometers arranged to respond to acceleration in three different axes, typically but not necessarily orthogonal axes, in three dimensional space.

Accelerometer 94 may be a MEMS accelerometer and correspond to the accelerometer disclosed in commonly-assigned U.S. Pat. No. 8,352,030 (Denison, et al.) or U.S. Pat. No. 8,386,042 (Yudovsky, et al.), both of which patents are incorporated herein by reference in their entirety. A pacemaker arrangement including a piezoelectric accelerometer for detecting patient motion is disclosed, for example, in U.S. Pat. No. 4,485,813 (Anderson, et al.) and U.S. Pat. No. 5,052,388 (Sivula, et al.), both of which patents are hereby incorporated by reference herein in their entirety. Examples of three-dimensional accelerometers used for sensing patient activity and/or posture are generally described in U.S. Pat. No. 5,593,431 (Sheldon), and U.S. Pat. No. 6,044,297 (Sheldon), both of which are hereby incorporated herein by reference in their entirety.

An accelerometer signal used for monitoring patient activity may be analyzed for providing a sensor-indicated pacing rate for controlling rate responsive cardiac pacing according to patient metabolic demand. An activity metric or index is derived from the accelerometer signal that is correlated to metabolic demand. Generally, the sensor-indicated pacing rate is computed from the activity metric within upper and lower pacing rate bounds to maintain a heart rate that meets the patient's metabolic need. Control of rate responsive pacing using an activity sensor is generally disclosed in commonly-assigned U.S. Pat. No. 7,031,772 (Condie, et al.), hereby incorporated herein by reference in its entirety.

An accelerometer signal may additionally or alternatively be used for monitoring patient activity for other patient monitoring, therapy control or diagnostic purposes. For example, it may be desirable to detect predetermined resting or active states of the patient to trigger monitoring of other physiological sensor signals, trigger therapies or adjustments to therapies, perform testing, etc. Accelerometer 94 may additionally or alternatively be used to determine patient posture, cardiac motion, respiratory motion or other physiological movement of a tissue, organ, limb, or whole body for use in monitoring the patient and/or controlling an IMD delivered therapy. The techniques disclosed herein for detecting loss of a reliable accelerometer signal are not limited to a particular use or application of the accelerometer signal.

Control module 80 may automatically adjust a therapy delivery rate and automatically adjust therapy control parameters based on motion monitoring performed using a single axis of accelerometer 94 or two or more axes that may be when accelerometer 94 is embodied as a multi-axis accelerometer. One or more axes signals may be selectable by control module 80 based on accelerometer selection criteria, which may include results from analyzing the accelerometer signal for detecting stiction. The control module 80 may be configured to evaluate different accelerometer axis signals to detect loss of a reliable accelerometer along a given axis. If an unreliable signal due to stiction is detected along a single axis and other axes are available, a patient activity metric or other motion metric used by control module 80 may be determined from a different accelerometer axis signal selected by control module 80.

Control module 80 includes a therapy control module for controlling therapy delivery module 84. Control module 80 may provide a corrective action in response to detecting reliable signal loss due to stiction of accelerometer 94 by adjusting a therapy control parameter based on an accelerometer signal and/or enabling, disabling or adjusting a therapy delivery function. For example, if stiction is detected in all available axes, rate-responsive pacing based on patient activity may be disabled, either permanently or temporarily until a reliable accelerometer signal is available.

Figure 4:
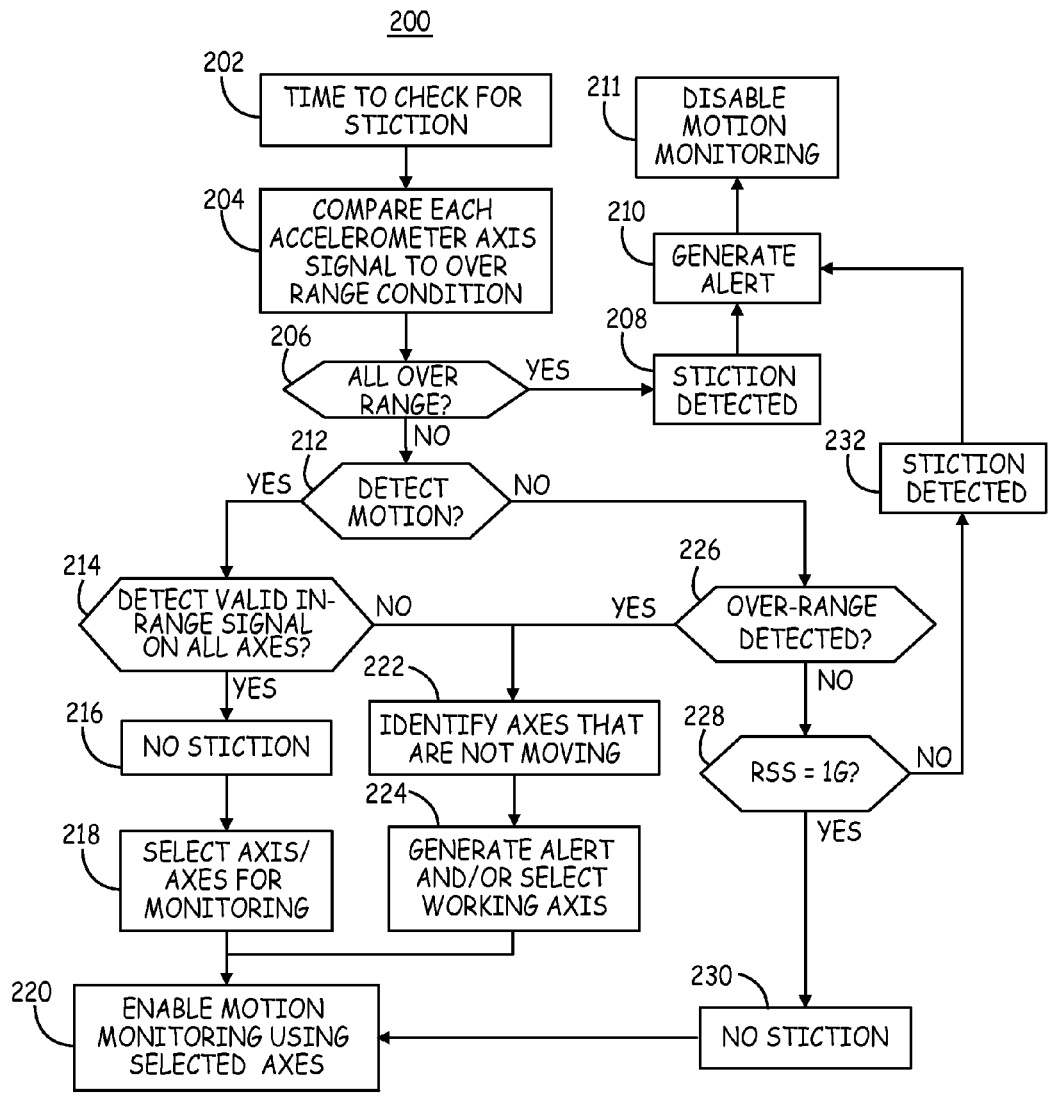
FIG. 4 is a flow chart of a method performed by the IMD of FIG. 1 for detecting stiction of an accelerometer according to one example.

FIG. 4 is a flow chart 200 of a method performed by control module 80 of IMD 16 for detecting stiction of accelerometer 94 according to one example. The process is started at block 202, which may be manually initiated by a user or performed automatically, e.g., on a scheduled periodic basis. In some examples, analysis of the accelerometer signal for detecting stiction may be performed when a sensor-indicated pacing rate or a motion metric determined from the accelerometer signal has remained at a substantially fixed value for more than a predefined time limit or is outside an expected range.

At block 204, the signal from each accelerometer axis is compared to an over range condition. In some cases, IMD 16 includes a single axis accelerometer so that a single signal is analyzed. In other cases, two or more axis signals are analyzed when IMD 16 includes a multi-axis accelerometer. The over range condition may be a maximum output signal, which may be a maximum positive or minimum negative signal, of the accelerometer. This over range condition is sometimes referred to as a "railed" condition when a movable component of the accelerometer is stuck at a maximum excursion point in the positive or negative direction. The over range condition may therefore include a threshold output signal, e.g., at or approaching a maximum range of the accelerometer in a positive or negative direction. The over range condition may additionally include a time interval requirement so that an over range signal amplitude is required to be sustained above (or below) the over range maximum positive (or minimum negative) threshold for a period of time.

If every accelerometer axis available is in an over range condition, as determined at block 206, stiction is detected at block 208. Control module 80 provides a response to detecting stiction, which may include generating an alert at block 210. The alert may be transmitted to external programmer 24 during a communication session to alert a user or technician that the accelerometer signal is not reliable for monitoring patient motion.

The response to stiction detection may additionally or alternatively include disabling motion monitoring at block 211. Certain functions of IMD 16 relating to patient monitoring or control of a delivered therapy that are based on the accelerometer signal may be disabled at block 211 by control module 80. For example, if the accelerometer signal is used for controlling rate-responsive pacing, rate-responsive pacing may be disabled automatically in response to detecting stiction in all accelerometer axes at block 208.

If all available accelerometer axes signals do not meet the over range condition, the signals are analyzed at block 212 to determine if motion is being detected from the accelerometer signal. Motion may be detected at block 212 if at least one accelerometer axis is producing a raw signal that is changing over time, e.g., over a predetermined number of sample points or predefined time interval. A threshold crossing, minimum difference, or percentage change in the raw accelerometer signal of at least one axis may be used to detect motion at block 212.

If motion is detected at block 212, control module 80 determines if all available accelerometer signals are producing a valid in-range signal at block 214 that varies over time indicating motion in all axes. If all axes are indicating motion, no stiction is detected. One or more axes may be selected for a monitoring application at block 218. Motion monitoring using the selected axis or axes of the accelerometer is enabled at block 220. Control of therapy delivery based on motion monitoring, e.g., rate-responsive pacing based on patient activity monitoring, may be enabled or, if previously enabled, remain ongoing at block 220.

If motion is detected at block 212, but not all axes are producing a valid in-range signal at block 214, one or more axes that are not detecting motion, i.e., producing a substantially unchanging or DC signal are identified at block 222. One or more axis may be in a stuck position that is not necessarily a railed position at a maximum excursion point. An alert may be generated at block 224 to notify a user that stiction is detected in at least one axis of the accelerometer. Additionally or alternatively, a working axis may be selected for motion monitoring at block 224. For example, the signal from a single axis may be used for determining activity counts used by control module 80 for determining patient activity or for determining other patient motion. If at least one axis is producing a time-varying motion signal, that axis may be selected for patient monitoring at block 224.

If motion is not being detected (block 212), control module 80 determines if any axis is producing a sustained over range signal at block 226. If one or more but not all axes are producing an over range signal ("yes" branch of block 226), control module 80 identifies the axis or axes that are producing an over range signal at block 222. An alert is generated and/or at least one working axis is selected for patient monitoring at block 224.

If none of the axes are producing an over range signal, but motion is not being detected, the DC signal being received from the accelerometer is compared to an expected 1 G signal. If no motion is detected but the accelerometer is functioning correctly, the root sum square of three orthogonal axes should approximate a 1 G signal corresponding to the force of gravity. If a valid 1 G DC signal is detected at block 228, no stiction is detected at block 230. Patient monitoring is performed according to an implemented protocol at block 220.

If the DC signal is not equal to a 1 G signal, within an acceptable error range, stiction may be occurring in one or more axes as detected at block 232. An alert may be generated at block 210 indicating that a loss of a reliable accelerometer signal. Patient monitoring may be disabled at block 211 or functions relying on the accelerometer signal may be limited or disabled.

Figure 5:
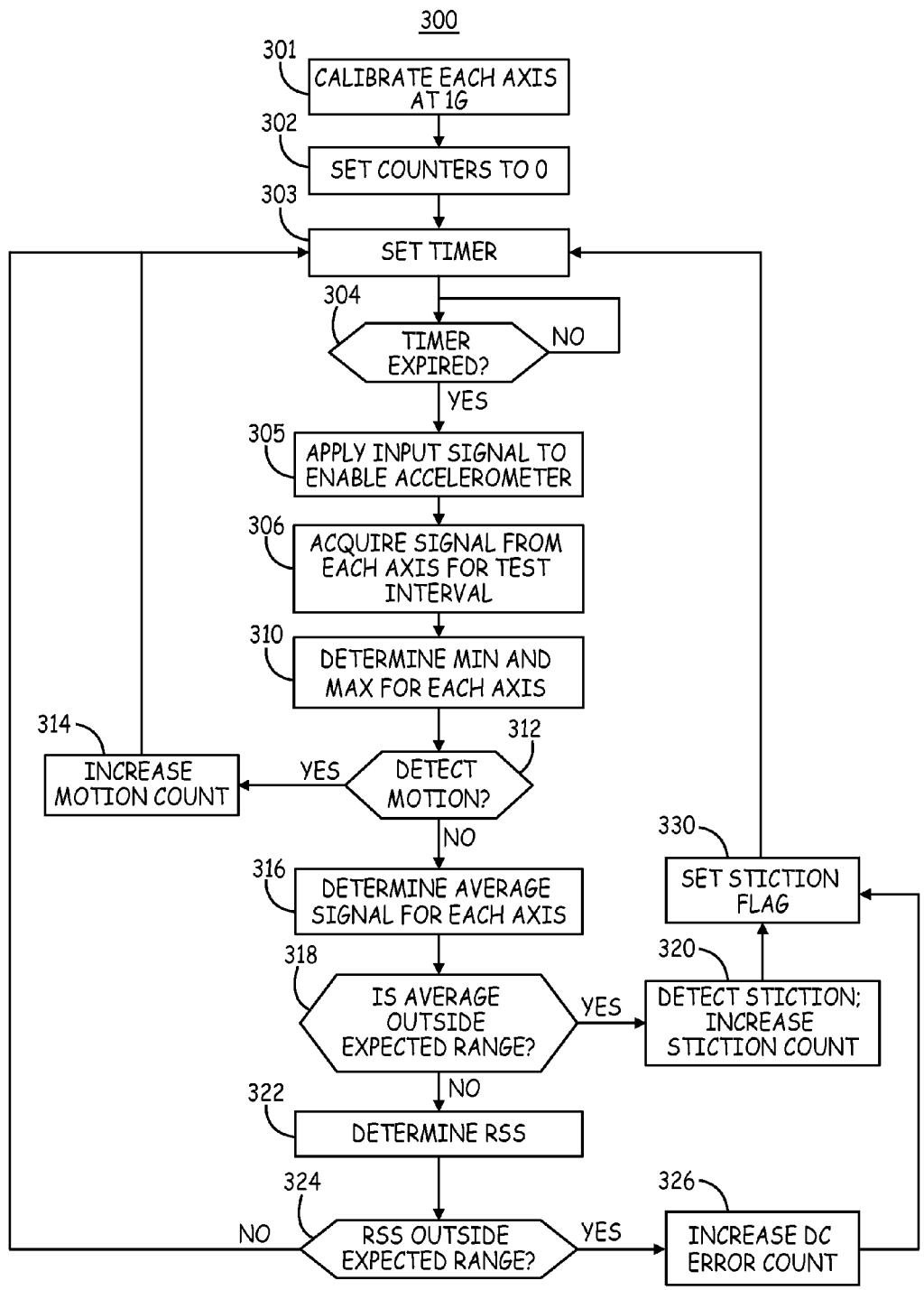
FIG. 5 is a flow chart of a method for detecting a loss of a reliable accelerometer signal in an IMD according to another example.

FIG. 5 is a flow chart 300 of a method for detecting a loss of a reliable accelerometer signal in an IMD according to another example. At block 301, each available axis of the accelerometer 94 is calibrated to determine each axis output signal under a 1 G condition. This output signal represents a maximum signal output signal expected from a given axis when no motion is being detected. Depending on the orientation of the accelerometer, a movable portion of a given accelerometer axis, when aligned with the direction of gravitational force, may be deflected to a maximum excursion in a positive or negative direction producing an expected maximum positive output signal or an expected minimum negative output signal when motion is not being detected. The output signal corresponding to 1 G is stored in memory 82 at block 301 and may be used by control module 80 to define an expected signal range when no motion is being detected in a given axis.

At block 302, a number of counters may be initialized to zero. A stiction counter may be established for each available accelerometer axis for counting the number of times stiction is detected in a given axis. Additionally, a DC error counter and a motion counter may be established for counting the number of times a DC error is identified but detection of stiction in a specific access is inconclusive and the number of times motion is detected based on any axis signal.

After calibration, diagnostic analysis of the accelerometer signal may be performed at any time after power source 96 is connected to control module 80 and accelerometer 94 of IMD 16, including during manufacturing, shipping, storage, and after implantation in a patient. Diagnostic analysis may be performed at regular intervals of time by setting a timer at block 303 and waiting for the timer to expire at block 304.

The diagnostic analysis may be performed any time, e.g., at regular time intervals or upon command, after power source 96 is coupled to accelerometer 94 and control module 80. Power source 96 provides an excitation signal to accelerometer 94 that enables accelerometer 94 to function in a normal operating state. In the normal operating state, accelerometer 94 is responsive to motion and produces a time-varying signal correlated to imparted motion when functioning properly. As such, analysis of the accelerometer signal when enabled for motion monitoring is performed by control module 80 without providing an electrostatic voltage signal or any other signal applied to intentionally cause movement of the accelerometer for artificially inducing a changing output signal for verifying accelerometer function. Accelerometer function is analyzed based on the accelerometer signal when the accelerometer 94 is exposed to whatever arbitrary motion may be present at the time of the diagnostic analysis.

Upon expiration of the timer, a signal is acquired from each available axis of the accelerometer for a predetermined analysis interval, e.g., one to five seconds. If the accelerometer is not already enabled, an excitation signal is applied to the accelerometer at block 305 to enable the accelerometer in a normal operating state to produce an output signal correlated to patient motion imposed on accelerometer 94. A signal is acquired from each available accelerometer axis over the predetermined analysis interval at block 306.

The axes signals of a multi-axis accelerometer may be evaluated simultaneously or sequentially. In the flow chart 300 of FIG. 5, each axis is evaluated simultaneously, however, it is recognized that the axes signals may be selected one at a time for the signal analysis that follows when a multi-axis accelerometer is being evaluated.

At block 310, the control module 80 determines the minimum and maximum raw signal values from each available axis signal over the analysis interval. The maximum and minimum for each axis are compared to motion detection criteria at block 312. If the axis signal is varying, the accelerometer is moving along that axis indicating proper accelerometer function. Detecting motion at block 312 may be based on determining the difference between the minimum and maximum raw signal values for each axis and comparing the differences to a predetermined threshold. If the difference between the minimum and maximum raw signal values during the analysis interval is greater than a predetermined difference threshold for any one of the available axes, motion is being detected from the accelerometer signal at block 312. The difference threshold may be a percentage of the total output signal range, e.g., 10% of the output signal range or other predetermined percentage or value. In various examples, the difference threshold is greater than approximately 30 mgRMS and may be in the range of 100 to 200 mgRMS.

As long as motion is detected from at least one axis signal, motion is detected and a motion counter included in control module 80 is increased by one count at block 314 indicating valid accelerometer function. The process returns to block 303 to reset the timer for scheduling the next diagnostic analysis.

If motion is not detected at block 312 in any of the accelerometer axes, the average signal amplitude is determined for each axis over the signal analysis interval at block 316. At block 318, the average signal amplitude for each axis is compared to the defined signal range that is expected when motion is not being detected. If the average signal for any axis is outside the expected range, as determined at block 318, a stiction count is increased at block 320 for that axis. For example, the average signal for a given axis may be compared to a maximum threshold and a minimum threshold. If the average signal amplitude is greater than the maximum threshold or less than the minimum threshold, the accelerometer may be railed at a maximum positive excursion or at a minimum negative excursion causing an over range condition in that axis or stiction may be preventing motion of the accelerometer in that axis and the moving portion is stuck in a position that is producing a signal outside the expected range.

The expected range may be defined based on the calibration performed at block 301. If no motion is being detected, the maximum expected absolute value of the output signal in any given axis should be 1 G if the accelerometer is working properly. If motion is not being detected and the absolute value of the average signal in a given axis is greater than the calibrated output signal at 1 G, stiction may be preventing movement of the accelerometer in that axis. A stiction counter for that axis is increased by one count at block 320. Control module 80 may include one stiction counter for each available accelerometer axis. The stiction counter is increased at block 320 for each axis in which the average signal is outside the expected output signal range corresponding to +1 G. Alternatively, a single stiction counter may be used to count the number of times stiction is detected in any axis.

If motion is not detected in any axis at block 312, but the average signal for each available axis is within the expected range at block 318, the control module 80 may determine the root sum square (RSS) of the accelerometer signal at block 322 if the accelerometer is configured as a three-dimensional accelerometer. The RSS is the square root of the sum of each of the squared orthogonal axis signals. The RSS may be computed from the average raw signal amplitude determined over the analysis interval for each axis. Alternatively, the RSS may be determined on a sample-by-sample basis from each axis signal and then averaged over the signal analysis interval to determine an average RSS.

If the RSS is outside an expected range corresponding to 1 G force, the control module 80 increases a DC error count by one at block 326. If motion is not detected, regardless of the orientation of a 3D accelerometer, the overall three-dimensional accelerometer signal output should correspond to a 1 G condition. If not, one or more axes of the accelerometer 94 may be stuck in a position that is producing a DC signal that is within an expected range but unreliable for motion monitoring. To detect a stiction condition is met when one or more axes are not moving but are in an in range position, it is recognized that the summation (of each axis signal squared) or the square root of the summation may be determined by control module 80 and compared to an appropriate threshold corresponding to a 1 G condition.

If the accelerometer is a three-dimensional accelerometer, control module 80 may include three counters for tracking the number of times stiction is detected in each of the three respective axes at block 320. In addition to those three stiction counters, control module 80 may include a DC error counter used to count the number of times the RSS (or the summation of the squared signal averages) is outside the expected range. The result of the RSS (or the summation of the squared signal averages) being outside an expected range is useful for detecting a possible stiction condition but may be inconclusive for determining which axis is experiencing stiction. As such, a single DC error counter is used to track the number of times signal error due to stiction is likely without specifying which axis or axes may be experiencing stiction.

The control module 80 may set a stiction flag at block 330 in response to detecting stiction and increasing the stiction count at block 320 or increasing the DC error count at block 326. A time and date stamp may be stored with the stiction flag to mark when stiction was first detected. The stiction flag may be reset to zero after a monitoring interval, e.g., after manufacturing and packaging is complete, after shipping, and at implant. As described below, the control module may compare counter values to failure criteria for predicting or detecting accelerometer failure and providing an appropriate response.

If the RSS (or summation of the squared signal averages) is within the expected range, the process returns to block 303 to restart the diagnostic analysis timer. The various counter values (i.e., the motion count, the stiction count for each axis individually or collectively, and the DC error count) are stored in memory 82 and may be used by control module 80 for automatically selecting an accelerometer axis for use in motion monitoring and/or automatically enabling or disabling motion monitoring and/or therapy delivery functions that are dependent on motion monitoring.

Figure 6:
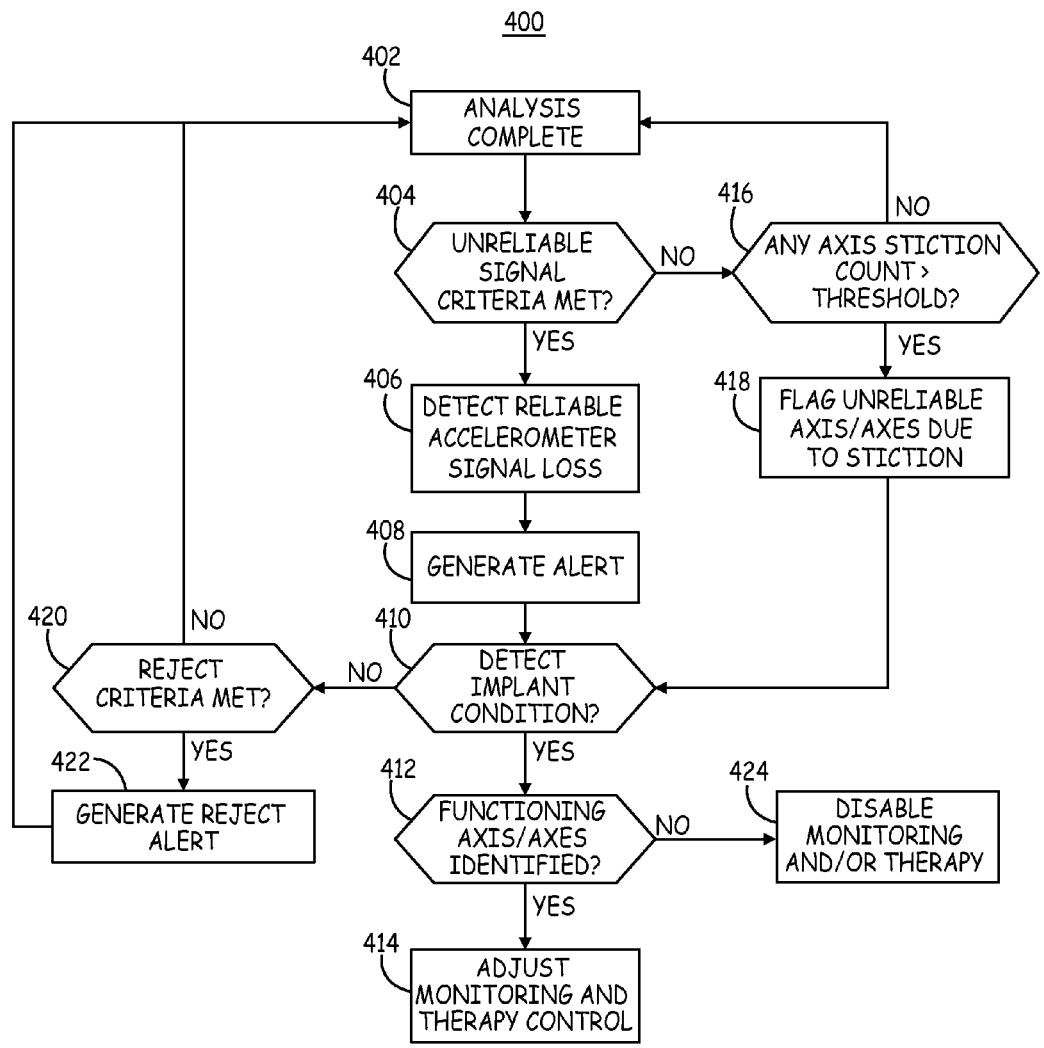
FIG. 6 is a flow chart of a method for controlling a corrective action in response to detecting stiction.

FIG. 6 is a flow chart 400 of a method for controlling a corrective action in response to stiction detection. After each diagnostic analysis is completed (block 402), e.g., according to the method shown in FIG. 5, control module 80 may determine if accelerometer rejection criteria are met at block 404. In other examples, the process shown by the flow chart of FIG. 6 may be performed less frequently than after every analysis interval, e.g., hourly, daily, weekly, etc. Detection of loss of a reliable accelerometer signal and responding thereto may require more than a single stiction event or a single DC error event in some examples. In order to detect loss of a reliable signal, control module 80 may compare the stiction counter value(s) and the DC error count value to respective unreliable signal criteria at block 404. Each stiction counter for each accelerometer axis and the DC error counter may be compared to respective individual unreliable signal thresholds, or a combined count from any combination of the counters may be compared to an overall unreliable signal threshold at block 404.

In some examples, if any one counter is greater than its respective threshold, reliable accelerometer signal loss is detected, and a response is provided. In this case, all available axes may be required for a particular monitoring application such as three-dimensional monitoring of patient posture. If any one axis is detected to reach an unreliable signal threshold, a signal loss response is provided. In other examples, all available axes may be required to reach an unreliable signal threshold in order to detect reliable signal loss due to stiction. For instance, if accelerometer 94 is a three-dimensional accelerometer, but only one axis is selected at a time for monitoring patient activity, as long as stiction has not been detected a threshold number of times in at least one axis, unreliable signal criteria are not met at block 404. In some examples, if the DC error count reaches a failure detection threshold, loss of a reliable accelerometer signal is detected at block 406.

In various examples, an unreliable signal detection threshold applied to a stiction count and an unreliable signal detection threshold applied to a DC error count may vary depending on the particular monitoring application. In some examples, occasional error in motion monitoring due to stiction may be tolerated. In other examples, error due to stiction may be less tolerated requiring more stringent failure detection. A lower count threshold may be used to detect an unreliable signal when motion error is less tolerated. As such, the unreliable signal criteria used to detect loss of a reliable signal may vary between embodiments.

If unreliable signal criteria are met at block 404, loss of a reliable accelerometer signal for motion monitoring is detected at block 406. A corrective action taken in response to reliable signal loss due to stiction detection may include generating an alert at block 408, which can be transmitted to a programmer or other device to notify the patient, clinician, technician, or other user of the reliable accelerometer signal loss the next time IMD 16 is interrogated or in communication with another device.

If unreliable signal criteria are not met at block 404, the stiction count for each available axis may be compared to an unreliable axis threshold at block 416. If the stiction count for a given axis reaches an unreliable axis threshold, but overall unreliable signal criteria are not met at block 404, the axis may be labeled as unreliable due to stiction. The label may remain stored in memory with a time and date stamp even if the same axis resulted in the motion counter to be increased during a subsequent diagnostic analysis. A given axis may experience stiction during an analysis interval causing the stiction count to be increased. The same axis may produce a motion signal during a later analysis interval causing the motion count to be increased. As such, the stiction or unreliable signal flag may be set at block 418 with a time and date stamp. In some instances, a given axis may be occasionally or intermittently dysfunctional due to stiction without the unreliable signal detection criteria being fully satisfied at block 404. The threshold used to set a stiction flag to label an individual axis at block 418 as unreliable may be the same, greater than or less than an unreliable signal criteria threshold applied to counters at block 404. To illustrate, if all three axes of a three dimensional accelerometer reach a stiction count of two, loss of a reliable accelerometer signal may be detected at block 406. If any one of the three axes has not reached a stiction count of two, reliable signal loss is not detected. If any of the three axes have reached a stiction count of one, however, a stiction flag may be set at block 418 to label each axis in which stiction has been detected.

At block 410, the control module 80 may determine if an implant condition is detected to control any additional response to the loss of reliable signal detection. An implant condition may be detected in response to an impedance measurement between electrodes 162 and 164, received physiological signals such as cardiac electrical signals, active therapy delivery, user-programmed parameter values, or other indication of the IMD 16 being implanted in the patient.

If an implant condition is not detected, control module 80 may determine if reject criteria are met at block 420. If loss of reliable signal was detected at block 406, reject criteria are also met at block 420. In other instances, reject criteria may be met when unreliable signal criteria are not met. Continuing the illustrative example given above, if the stiction flag has been set at block 416 for any of the three axes, the reject criteria may be met at block 420 even though unreliable signal detection criteria have not been met. The reject criteria may be used to identify accelerometers that are expected to have a higher likelihood of experiencing stiction after implant. Any accelerometer in which stiction has been detected at least once prior to implantation may be predicted as being more likely to produce an unreliable signal after implant than an accelerometer in which stiction has never been detected prior to implantation.

If reject criteria are met, a corrective action may include generating a reject alert at block 422. At any time prior to implant, the external programmer or other device configured to communicate with IMD 16 may receive the reject alert thereby notifying a technician or other user that the accelerometer may not meet reliability requirements for implanting in a patient. The inability of the accelerometer to overcome static forces leading to stiction detection by control module 80 may be caused by damage to anti-stick coatings used on MEMS elements due to an excessive shock, repetitive shocks, or other manufacturing defect.

Additional testing and analysis may be performed before shipping or implantation to verify accelerometer performance. In some examples, the accelerometer 94 or IMD 16 may be rejected as being unsuitable for implantation in response to the reject criteria being met.

In some cases, reject criteria may be based on the motion count in addition to the stiction count and the DC error count. For example, prior to implant, a high motion count may indicate that the accelerometer has been exposed to significant impact, shaking or other physical forces that could damage circuitry or compromise IMD functionality. A very high or a very low motion count in a particular IMD out of a manufacturing lot may be an indicator that the accelerometer 94 or other electronics of IMD 16 should undergo further testing or evaluation prior to advancing through manufacturing processes, shipping or implant. As such, an average or range of motion counts for each accelerometer in a manufacturing lot may be determined and the motion count of an individual accelerometer (or IMD) may be compared to an upper and lower threshold set based on the average or range of motion counts for the lot. In other examples, a motion count that indicates regular normal functioning of the accelerometer is an indicator that the accelerometer is acceptable and working properly and can be used to confirm an acceptable device prior to implant as well as confirm a properly functioning accelerometer after implant when selecting programmable monitoring and therapy delivery functions or troubleshooting IMD functions.

If an implant condition is detected at block 410, control module 80 may adjust monitoring and/or therapy delivery functions at blocks 412 and 414 in response to detecting reliable accelerometer signal loss at block 406 or an unreliable axis flag being set at block 416. If an axis can be identified that has not reached unreliable signal criteria, that axis (or axes) may be selected for motion monitoring by control module 80. In some examples, an axis that does not have a stiction flag set, has a highest motion count and/or lowest stiction count may be identified at block 412 as a reliable axis for motion monitoring.

At block 414, control module 80 may adjust monitoring and/or therapy delivery functions based on whether an reliable signal loss alert has been generated (block 408), whether stiction flags have been set (block 418), and an axis or axes identified at block 412. For example, if an alert has not been generated at block 408 but a stiction flag has been set, control module 80 may select one or more axes identified at block 412 to perform motion monitoring in the patient. Patient monitoring may continue using the selected axis/axes.

A therapy delivery function that is dependent on motion monitoring, e.g., rate responsive pacing, may be enabled at block 414 as long as a reliable axis is identified. Alternatively, if stiction flags are set at block 418, motion monitoring may continue using a selected axis/axes, but a therapy delivery function dependent on motion monitoring may be temporarily disabled until reliable accelerometer function can be verified. Accelerometer function may be verified manually by a user based on a review of motion data or automatically by control module 80 if the motion count is increased based on a given axis signal at a time after a stiction flag has been set for that axis, indicating that a temporary stiction condition may no longer be present.

If a reliable signal loss alert has been generated at block 408 such that no axis is identified as a reliably functioning axis at block 412, motion monitoring and/or therapy delivery functions dependent on motion monitoring may be automatically disabled by control module 80 at block 424. In some cases, motion monitoring may continue but is not used for controlling therapy delivery. Motion data may be reviewed by a clinician, technician or other expert to verify accelerometer function to override an automatic disabling of a therapy delivery function, re-program IMD 16 without motion monitoring functions, or guide a decision to replace IMD 16.

Thus, various embodiments of a medical device and method have been described for automatically detecting loss of a reliable accelerometer signal in a medical device. However, one of ordinary skill in the art will appreciate that various modifications may be made to the described embodiments without departing from the scope of the following claims.

The invention claimed is:

1. A method, comprising:
applying a normal input signal to a micro-electrical mechanical systems (MEMS) sensor to enable the MEMS sensor to function in a normal operating state of producing a time-varying sensor signal that is correlated to physical motion that is imposed on the sensor, wherein the normal input signal is configured not to cause motion of the MEMS sensor;
determining by a control module of a medical device a signal amplitude of the sensor signal produced by the MEMS sensor enabled by the normal input signal;
comparing the signal amplitude to a stiction detection condition;
detecting stiction of the MEMS sensor in response to the signal amplitude meeting the stiction detection condition; and
automatically providing a corrective action in response to detecting the stiction.

2. The method of claim 1, wherein:
determining the signal amplitude comprises acquiring the sensor signal over an analysis interval and determining the signal amplitude as an average amplitude of the sensor signal over the analysis interval; and
comparing the signal amplitude to a stiction detection condition comprises comparing the average amplitude to a threshold.

3. The method of claim 1, further comprising:
acquiring a sensor axis signal for each of a plurality of sensor axes over an analysis interval;
wherein determining the signal amplitude comprises:
determining an average of each sensor axis signal over the analysis interval; and
determining a summation of each of the averages squared.

4. The method of claim 1, further comprising:
increasing a counter in response to detecting the stiction, and
providing the corrective action comprises generating an alert in response to the counter reaching a threshold.

5. The method of claim 1, wherein providing the corrective action comprises selecting one of a plurality of axes of the MEMS sensor in response to detecting stiction in a different one of the plurality of axes of the MEMS sensor for monitoring motion of a patient.

6. The method of claim 1, wherein providing the corrective action comprises at least one of generating an alert, automatically adjusting a monitoring control parameter of the medical device and automatically adjusting a therapy delivery control parameter of the medical device.

7. The method of claim 1, further comprising:
wherein comparing the signal amplitude to the stiction detection condition comprises:
establishing a stiction detection counter for each one of a plurality of axes;
determining the signal amplitude from each of a plurality of axes of the MEMS sensor;
comparing the signal amplitude for each of the plurality of axes to a stiction detection threshold;
in response to the signal amplitude for any one of the plurality of axes meeting the stiction detection threshold, incrementing a stiction detection counter for a respective one of the plurality of axes;
wherein detecting stiction comprises comparing each of the stiction detection counters to a count threshold and detecting stiction in response to a required number of the stiction detection counters reaching the count threshold.

8. The method of claim 1, further comprising:
acquiring an axis signal for each of a plurality of axes of the MEMS sensor over an analysis interval;
determining a difference for each axis signal between a maximum and a minimum of the respective axis signal;
compare the difference to a motion threshold;
detect motion in response to at least one of the differences being greater than the motion threshold;
withholding the comparing of the signal amplitude to a stiction detection condition in response to motion being detected;
in response to motion not being detected, determining the signal amplitude by determining an average amplitude over the analysis interval for each of the axis signals for each of the plurality of axes;
comparing the average amplitude determined for each of the plurality of axes to a stiction threshold;
detecting stiction in response to at least one of the average amplitudes meeting the stiction threshold;
in response to none of the average amplitudes meeting the stiction threshold, determining a summation of each of the average amplitudes squared;
comparing one of the summation and a square root of the summation to an error threshold; and
detecting stiction in response to one of the summation and the square root of the summation meeting the error threshold.

9. The method of claim 1, wherein:
determining the signal amplitude comprises determining a signal amplitude for each of a plurality of signal axes of the MEMS sensor;
comparing the signal amplitude to stiction detection condition comprises comparing the signal amplitude for each of the plurality of signal axes to motion detection criteria and comparing the signal amplitude for each of the plurality of signal axes to the stiction detection criteria if none of the signal amplitudes for each of the plurality of signal axes meet the motion detection criteria;
wherein providing the corrective action comprises:
responsive to the signal amplitude of a given one of the plurality of signal axes meeting the motion detection criteria, incrementing a motion count for the given one of the plurality of signal axes;
responsive to the signal amplitude for a given one of the plurality of signal axes meeting the stiction detection criteria, incrementing a stiction count for the given one of the plurality of signal axes; and selecting one of the plurality of axes for monitoring motion in a patient based on the motion counts for each of the plurality of signal axes and the stiction counts for each of the plurality of signal axes.

10. A method, comprising:
determining by a control module of a medical device a signal amplitude of a sensor signal produced by a micro-electrical mechanical systems (MEMS) sensor;
comparing the signal amplitude to a stiction detection condition;
detecting stiction of the MEMS sensor in response to the signal amplitude meeting the stiction detection condition;
acquiring the sensor signal over an analysis interval;
detecting motion in response to the sensor signal acquired over the analysis interval;
withholding the comparing of the signal amplitude to the stiction detection condition in response to the motion being detected; and
automatically providing a corrective action in response to detecting the stiction.

11. The method of claim 10, wherein detecting motion comprises:
determining a signal amplitude difference during the analysis interval;
comparing the difference to a motion detection threshold; and
detecting motion in response to the difference exceeding the motion detection threshold.

12. The method of claim 10, further comprising:
incrementing a motion count in response to detecting motion;
comparing the motion count to a threshold; and
generating an alert in response to the motion count exceeding a threshold.

13. A medical device, comprising:
a micro-electrical mechanical system (MEMS) sensor configured to produce a sensor signal correlated to motion of the medical device; and
a control module configured to:
apply a normal input signal to the MEMS sensor to enable the MEMS sensor to function in a normal operating state of producing the sensor signal as a time-varying signal that is correlated to physical motion that is imposed on the sensor, wherein the normal input signal is configured not to cause motion of the MEMS sensor;
determine a signal amplitude of the sensor signal;
compare the signal amplitude to a stiction detection condition;
detect stiction of the MEMS sensor in response to the signal amplitude meeting the stiction detection condition; and
provide a corrective action in response to detecting the stiction.

14. The device of claim 13, wherein the control module is further configured to:
determine the signal amplitude by acquiring the sensor signal over an analysis interval and determining the signal amplitude as an average amplitude of the sensor signal over the analysis interval; and
compare the signal amplitude to a stiction detection condition by comparing the average amplitude to a threshold.

15. The device of claim 13, wherein the control module is further configured to:
acquire an axis signal for each of a plurality of axes of the MEMS sensor over an analysis interval;
determine the signal amplitude by:
determining an average of each axis signal over the analysis interval; and
determining a summation of each of the averages squared.

16. The device of claim 13, wherein the control module is further configured to:
increase a counter in response to detecting the stiction, and
provide the corrective action by generating an alert in response to the counter reaching a threshold.

17. The device of claim 13, wherein the control module is configured to provide the corrective action by selecting one of a plurality of axes of the MEMS sensor in response to detecting stiction in a different one of the plurality of axes of the MEMS sensor for monitoring motion of a patient.

18. The device of claim 13, wherein the control module is configured to provide the corrective action by at least one of: generating an alert, automatically adjusting a monitoring control parameter of the medical device and automatically adjusting a therapy delivery control parameter of the medical device.

19. The device of claim 13, wherein the control module is further configured to:
compare the signal amplitude to the stiction detection condition by:
establishing a stiction detection counter for each one of a plurality of axes of the MEMS sensor;
determining a signal amplitude from each of a plurality of axes;
comparing the signal amplitude for each of the plurality of axes to a stiction detection threshold;
in response to the signal amplitude for any one of the plurality of axes meeting the stiction detection threshold, incrementing a stiction detection counter for the respective one of the plurality of axes; and
detect stiction by comparing each of the stiction detection counters to a count threshold and detecting stiction in response to a required number of the stiction detection counters reaching the count threshold.

20. The device of claim 13, wherein the control module is further configured to:
acquire an axis signal for each of a plurality of axes of the MEMS sensor over an analysis interval;
determine a difference for each axis signal between a maximum and a minimum of the respective axis signal;
compare the difference to a motion threshold;
detect motion in response to at least one of the differences being greater than the motion threshold;
withhold the comparing of the signal amplitude to a stiction detection condition in response to motion being detected;
in response to motion bot being detected, determine the signal amplitude by determining an average amplitude over the analysis interval for each of the axis signals;
compare the average amplitude determined for each of the plurality of axes to a stiction threshold;
detect stiction in response to at least one of the average amplitudes meeting the stiction threshold;
in response to none of the average amplitudes meeting the stiction threshold, determine a summation of each of the average amplitudes squared;
compare one of the summation and a square root of the summation to an error threshold; and
detect stiction in response to one of the summation and the square root meeting the error threshold.

21. The device of claim 13, wherein the control module is further configured to:

determine the signal amplitude by determining a signal amplitude for each of a plurality of signal axes of the MEMS sensor;

compare the signal amplitude to stiction detection condition by comparing the signal amplitude for each of the plurality of signal axes to motion detection criteria and comparing the signal amplitude for each of the plurality of signal axes to the stiction detection condition in response to none of the signal amplitudes for each of the plurality of signal axes meeting the motion detection criteria; and provide the corrective action by:

responsive to the signal amplitude of a given one of the plurality of signal axes meeting the motion detection criteria, incrementing a motion count for the given one of the plurality of signal axes;

responsive to the signal amplitude for a given one of the plurality of signal axes meeting the stiction detection criteria, incrementing a stiction count for the given one of the plurality of signal axes; and selecting one of the plurality of axes for monitoring motion in a patient based on the motion counts for each of the plurality of signal axes and the stiction counts for each of the plurality of signal axes.

22. A medical device, comprising:

a micro-electrical mechanical system (MEMS) sensor configured to produce a sensor signal correlated to motion of the medical device; and a control module configured to:

determine a signal amplitude of the sensor signal;

compare the signal amplitude to a stiction detection condition;

detect stiction of the MEMS sensor in response to the signal amplitude meeting the stiction detection condition;

acquire the sensor signal over an analysis interval;

detect motion in response to the sensor signal acquired over the analysis interval;

withhold the comparing of the signal amplitude to the stiction detection condition in response to the motion being detected; and provide a corrective action in response to detecting the stiction.

23. The device of claim 22, wherein the control module is configured to detect motion by:

determining a signal amplitude difference during the analysis interval;

comparing the difference to a motion detection threshold; and detecting motion in response to the difference exceeding the motion detection threshold.

24. The device of claim 22, wherein the control module is further configured to:

increment a motion count in response to detecting motion;

compare the motion count to a threshold; and generate an alert in response to the motion count exceeding a threshold.

25. A non-transitory computer readable storage medium comprising a set of instructions that, when executed by a control module of a medical device comprising a micro-electrical mechanical system (MEMS) sensor, cause the device to:

apply a normal input signal to the MEMS sensor to enable the MEMS sensor to function in a normal operating state of producing a time-varying sensor signal that is correlated to physical motion that is imposed on the sensor, wherein the normal input signal is configured not to cause motion of the MEMS sensor;

determine a signal amplitude of a sensor signal produced by the MEMS sensor;

compare the signal amplitude to a stiction detection condition;

detect stiction of the MEMS sensor in response to the signal amplitude meeting the stiction detection condition; and provide a corrective action in response to detecting the stiction.

* * * * *

UNITED STATES PATENT AND TRADEMARK OFFICE
CERTIFICATE OF CORRECTION

| | | |
|---|---|---|
| PATENT NO. | : 9,522,276 B2 | Page 1 of 1 |
| APPLICATION NO. | : 14/603070 | |
| DATED | : December 20, 2016 | |
| INVENTOR(S) | : Shen et al. | |

It is certified that error appears in the above-identified patent and that said Letters Patent is hereby corrected as shown below:

In the Claims

Column 20, Lines 52-54, delete "in response to motion bot being detected, determine the signal amplitude by determining an average amplitude over the analysis interval for each of the axis signals;" and insert in place thereof -- in response to motion not being detected, determine the signal amplitude by determining an average amplitude over the analysis interval for each of the axis signals --.

Signed and Sealed this
Twenty-third Day of May, 2017

Michelle K. Lee
*Director of the United States Patent and Trademark Office*